(12) United States Patent
Shaw et al.

(10) Patent No.: US 9,814,609 B2
(45) Date of Patent: Nov. 14, 2017

(54) MEDICAL DEVICE FIXATION ANCHOR SUITED FOR BALLOON EXPANDABLE STENTS

(75) Inventors: Edward E. Shaw, Flagstaff, AZ (US); John R. Daugherty, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 281 days.

(21) Appl. No.: 12/817,234

(22) Filed: Jun. 17, 2010

(65) Prior Publication Data

US 2010/0324665 A1  Dec. 23, 2010

Related U.S. Application Data

(60) Provisional application No. 61/187,689, filed on Jun. 17, 2009.

(51) Int. Cl.
| | | |
|---|---|---|
| *A61F 2/82* | (2013.01) | |
| *A61F 2/91* | (2013.01) | |
| A61F 2/958 | (2013.01) | |
| A61F 2/848 | (2013.01) | |

(52) U.S. Cl.
CPC ............ *A61F 2/91* (2013.01); *A61F 2/958* (2013.01); *A61F 2002/8483* (2013.01); *A61F 2220/005* (2013.01); *A61F 2220/0016* (2013.01); *A61F 2220/0058* (2013.01)

(58) Field of Classification Search
CPC .................................. A61F 2/06; A61F 2/82
USPC ......................................................... 623/1.15
See application file for complete search history.

(56) References Cited

U.S. PATENT DOCUMENTS

| | | | |
|---|---|---|---|
| 5,423,851 A | 6/1995 | Samuels | |
| 6,007,558 A | 12/1999 | Ravenscroft et al. | |
| 6,042,605 A | 3/2000 | Martin et al. | |
| 6,361,637 B2 | 3/2002 | Martin et al. | |
| 6,517,573 B1* | 2/2003 | Pollock et al. | 623/1.15 |
| 6,520,986 B2 | 2/2003 | Martin et al. | |
| 2003/0220683 A1* | 11/2003 | Minasian et al. | 623/1.15 |
| 2004/0010312 A1* | 1/2004 | Enayati | 623/17.11 |
| 2008/0132996 A1* | 6/2008 | Drasler | A61F 2/07 623/1.15 |
| 2009/0082847 A1 | 3/2009 | Zacharias et al. | |

FOREIGN PATENT DOCUMENTS

| | | |
|---|---|---|
| CN | 1555769 | 12/2004 |
| CN | 2887334 | 4/2007 |
| CN | 101031254 | 9/2007 |
| CN | 101234046 | 8/2008 |
| CN | 101351168 | 1/2009 |
| EP | 732088 | 9/1996 |
| EP | 1880693 | 1/2008 |
| JP | 2005-525910 | 9/2005 |
| WO | 01/76509 | 10/2001 |
| WO | 2005/099627 | 10/2005 |
| WO | 2005/102214 | 11/2005 |

OTHER PUBLICATIONS

International Search Report and Written Opinion, PCT/US2010/001748, dated Aug. 4, 2010, 13 pages.
International Search Report and Written Opinion, PCT/US2010/001765, dated Oct. 5, 2010, 14 pages.

* cited by examiner

*Primary Examiner* — Matthew Schall

(57) ABSTRACT

A balloon expandable anchor for a medical device. The anchor barb is contained within the device compacted delivery profile and is balloon expanded to rest outside of the expanded device profile.

11 Claims, 3 Drawing Sheets

MEDICAL DEVICE FIXATION ANCHOR SUITED FOR BALLOON EXPANDABLE STENTS

CROSS REFERENCE TO RELATED APPLICATIONS

This application claims priority to provisional application U.S. Ser. No. 61/187,689, filed Jun. 17, 2009.

BACKGROUND OF THE INVENTION

Field of the Invention

The invention relates to a medical device fixation anchor and in particular with an anchor that is suitable for use with a balloon expandable stent.

Discussion of the Related Art

Various medical devices require some form of fixation or anchoring to a targeted site. Common anchoring means include barbs, hooks, sutures, or other features used to attach a device to the surrounding anatomy. Some examples of devices requiring a means to anchor include vena-cava filters, stents, stent grafts, bile/urinary duct stents, intestinal/gastro stents and liners, occluders, electrophysiological leads, various monitors or diagnostic devices, central venous catheters, and other devices as commonly know in the art. Many of these devices incorporate a balloon expandable component that is expanded to bear against the surrounding anatomy, thus providing an anchoring means. The degree of positional anchoring of the medical device is normally dependent upon the degree of "over-expansion" of the balloon expandable component. When over-expanded, the expandable portion is aggressively forced against the surrounding anatomy, affecting a frictional or "interference-fit" means of anchoring. If the degree of over-expansion is excessive, the surrounding anatomy can be damaged. Conversely, if the degree of over-expansion is minimal, the device may dislodge due to poor anchoring.

An improved means of anchoring a balloon expandable component incorporates expandable anchors or barbs. These expandable anchors eliminate the need for aggressive over-expansion and provide a degree of anchoring if the over-expansion is minimal. An improved, balloon expandable anchor can also improve the retention of the expandable component to the balloon. The improved balloon expandable anchors can be contained within the profile of the expandable device, so they do not interfere with the delivery of the device.

SUMMARY OF THE INVENTION

An embodiment of the present invention includes a medical fixation device, comprising:
a medical fixation device having
 a balloon expandable anchor with a device attachment portion, an expansion bearing portion and a barb portion;
the anchor expansion bearing portion being positioned between the anchor device attachment portion and the anchor barb portion;
the device attachment portion being coupled to an expandable medical device having a first compacted profile and a second expanded profile;
the anchor barb portion positioned within the first compacted profile; and the anchor being deformed to extend the anchor barb portion outside the second expanded profile.

Additional features and advantages of the invention will be set forth in the description or may be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, to illustrate embodiments of the invention, and together with the description serve to explain the principles of the invention.

DETAILED DESCRIPTION OF THE ILLUSTRATED EMBODIMENTS

The invention is directed to a medical device anchoring or fixation means that enhances the ease of initial compaction and subsequent device deployment.

Figure 1A:
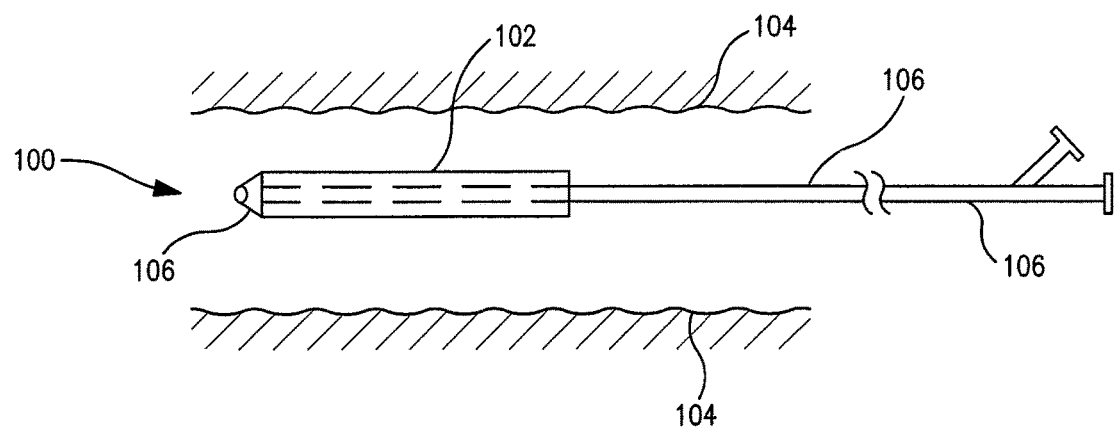
FIG. 1A is a partial side view of a medical device prior to implantation. The medical device shown is a balloon expandable stent surrounding a balloon and a delivery catheter.
Figure 1B:
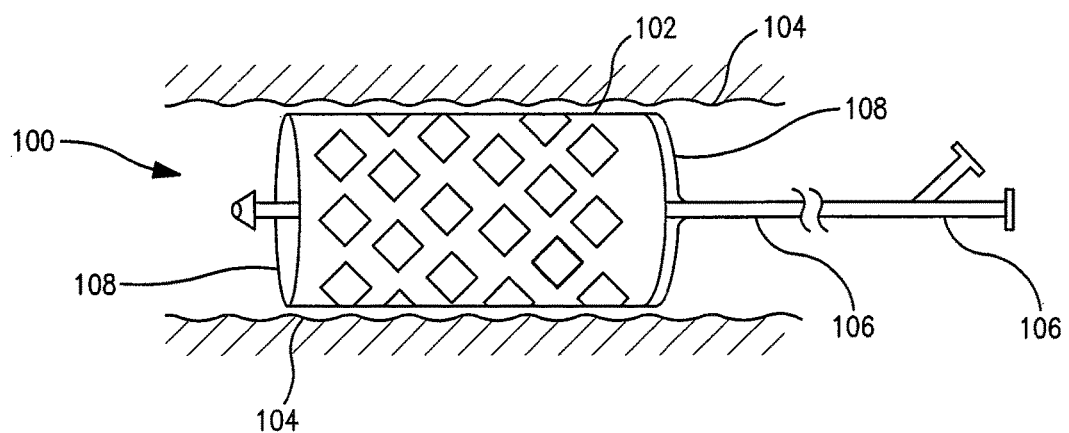
FIG. 1B is a partial side view of a medical device that has been balloon expanded.

FIGS. 1A and 1B show a general example of a medical device delivery sequence. Shown in partial side view, FIG. 1A is a compacted medical device 100. The specific medical device shown is a balloon expandable stent 102. The medical device is shown positioned within a lumen 104. The balloon expandable stent 102 is shown compacted onto a balloon (not shown) and delivery catheter 106.

Shown in partial side view, FIG. 1B is the medical device 100 in an expanded state. Shown are a balloon expandable stent 102 (shown in an expanded shape), an expanded balloon 108 and the delivery catheter 106. In a typical procedure, the internal balloon pressure expands a malleable stent (or other device), forcing the malleable stent into contact with the surrounding anatomy or lumen wall 104. The magnitude of balloon pressure normally dictates the outer profile of the stent and the degree of over-expansion or embedding into a vessel wall.

Figure 2A:
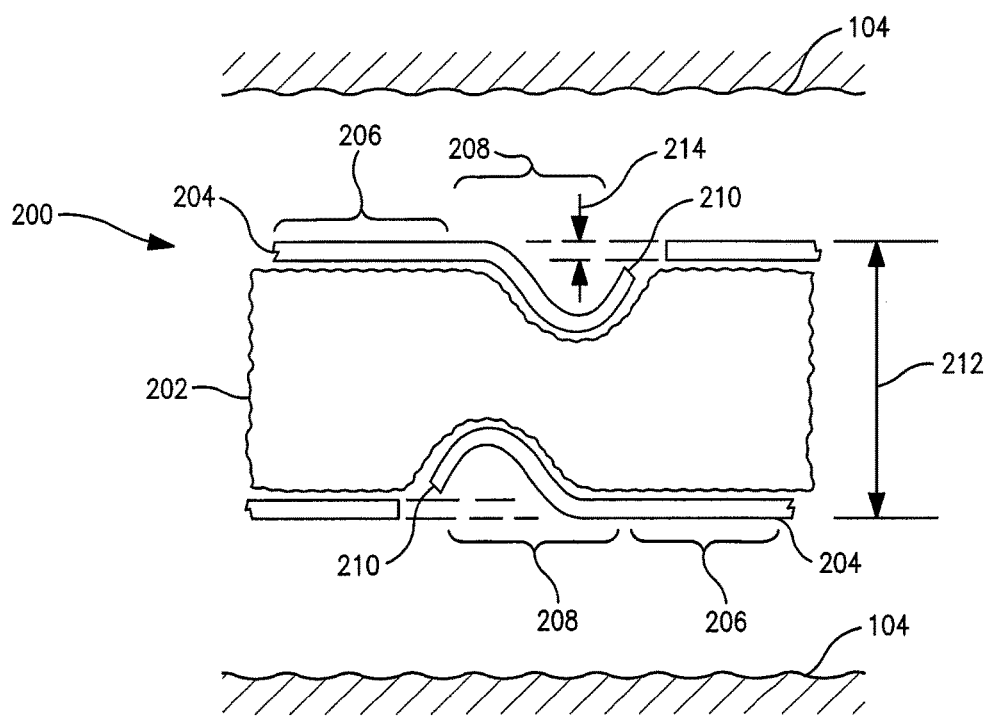
FIGS. 2A and 2B are partial side views of an improved balloon expandable anchor showing the anchor barb contained within a first compacted device profile and shown outside of an expanded device profile.
Figure 2B:
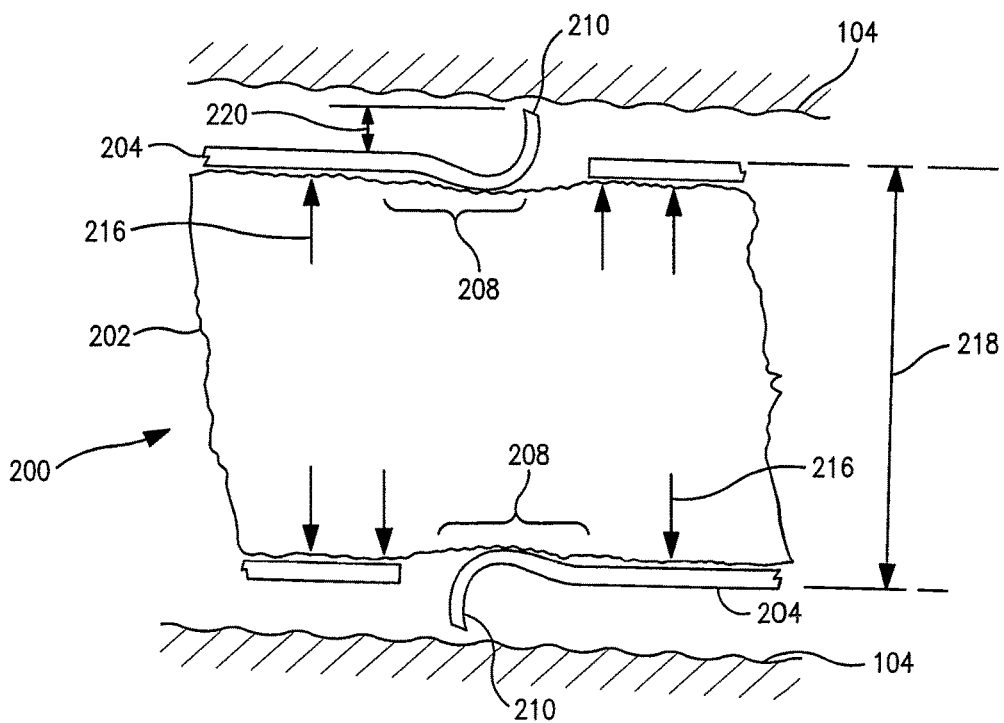

FIGS. 2A and 2B are partial side views of an improved balloon expandable anchor. The expandable medical device 200 is shown within a lumen 104 and surrounding an inflatable balloon 202. The medical device has an expandable anchor 204 having a device attachment portion 206 (used to couple the anchor to a medical device), an expansion bearing portion 208 and a barb portion 210. As shown in FIG. 2A, the medical device 200 is shown having a first compacted profile 212. As shown, the anchor barb portion 210 is contained within 214 the first compacted profile 212. An expansion bearing portion 208 can be configured in a variety of ways and may include curved, protruding, flat, or any other profile that will result in the barb portion 210 being contained within the first compacted profile 212.

As shown in FIG. 2B, the internal balloon pressure 216 forces the medical device 200 to expand to a second expanded profile 218. Upon expansion, the balloon 202 contacts the expansion bearing portion 208 forcing the expandable anchor 204 to expand so that the barb portion 210 extends outside 220 of the second expanded profile 218.

Figure 3:
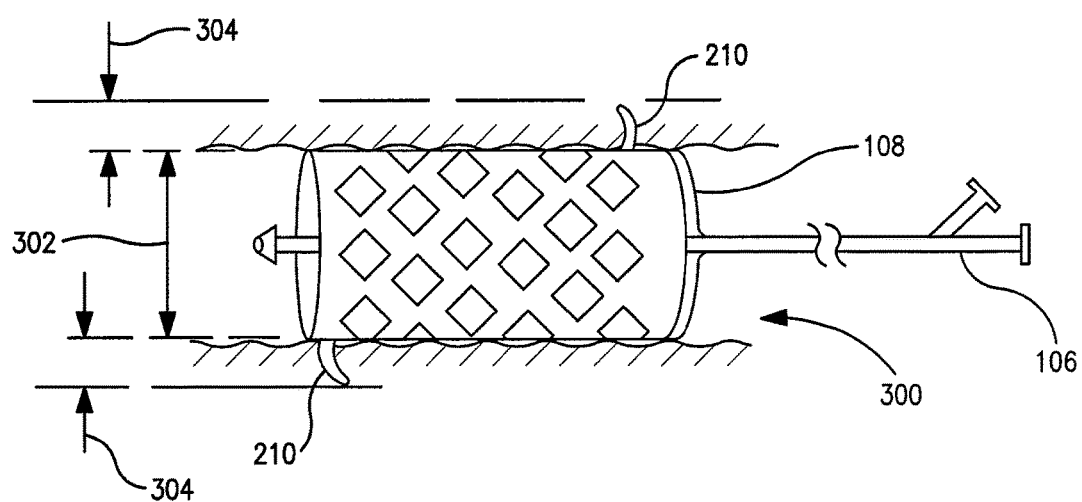
FIG. 3 is a partial side view of a balloon expanded medical device having two anchor barbs extending outside of a device expanded profile.

Shown in FIG. 3 is a partial side view of a balloon expandable medical device 300, surrounding an expanded balloon 108 and a delivery catheter 106. The expanded medical device 300 is shown having a second expanded profile 302 and two anchor barb portions 210. The two anchor barb portions 210 are shown extending outside 304 of the second expanded profile 302.

Although shown with expanding balloons, the expandable anchors of the present invention may also be used with other means to expand, such as mechanical bow-arms, expandable "Chinese lanterns", expandable baskets, or other expanding devices or materials.

Balloon expandable anchors can comprise commonly known materials (or combinations of materials) used in the manufacture of balloon expandable stents. Typical materials include 316L stainless steel, cobalt-chromium-nickel-molybdenum-iron alloy ("cobalt-chromium"), other cobalt alloys such as L605, tantalum, malleable Nitinol, or other bio-compatible malleable metals. Other suitable materials include specialized malleable polymers, malleable bio-absorbable materials, and the like.

Typical methods used in the assembly of anchors to medical devices include commonly known techniques used to attach two or more components. Examples of permanent attachments include the use of glues, adhesives, welds, insert molding, heavy press-fits, one-way snap or lock features, pressed pins, heat staking, and rivets. Examples of semi-permanent attachments or those that require a tool to separate the components include screws, threaded fasteners, snap-rings, and snap-fits. Examples of releasable attachments or those that can be separated by hand without the use of an additional tool include snap-fits, twist lock features, push to release features, squeeze to release features, slide levers, latches, and light press-fits.

Anchors can have various cross-sectional profiles such as circular, oval, rectangular, or other polygon shapes. Anchors can also incorporate external lubricious layers, lubricious coatings, or lubricious wrappings to minimize friction. Anchors can also incorporate therapeutic agents tailored for specific biological results. Anchors can also include radiopaque markers or radiopaque intensifiers.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A medical device, comprising:
   an expandable body configured to be deployed in a body of a patient, having an inner lumen, and configured to transition from a first compacted profile to a second expanded profile upon application of an extrinsic expansion force to the expandable body, the first compacted profile including the inner lumen defining an inner boundary of the expandable body;
   an expandable anchor having a device attachment portion directly coupled to a tubular body, a barb portion, and an expansion bearing portion positioned between the device attachment portion and the barb portion;
   wherein prior to the application of the extrinsic expansion force, the barb portion is positioned within the first compacted profile and the expansion bearing portion extends radially inward of the inner boundary of the expandable body such that the expansion bearing portion is configured to be engaged by the extrinsic expansion force to extend the barb radially outward from the expandable body of the medical device in the second expanded profile.

2. The medical device of claim 1 wherein the barb portion is metal.

3. The medical device of claim 1 wherein the expansion bearing portion is linear.

4. The medical device of claim 1 wherein the expansion bearing portion is non-linear.

5. The medical device of claim 1, wherein the extrinsic expansion force is an inflatable balloon.

6. A medical device system, comprising:
   an expansion device operable to be radially expandable to an expanded state; and
   an expandable medical device having an inner lumen and mounted to the expansion device for deployment of the expandable medical device, the expandable medical device including an expandable anchor having a barb portion and an expansion bearing portion, the expandable medical device having an outer surface and an inner surface, the expandable medical device having a first compacted profile in which the expansion bearing portion extends inward relative to the inner lumen and, upon application of an extrinsic force by the expansion device, a second expanded profile, the first compacted profile including the barb portion being positioned within the first compacted profile and extended from the medical device in the second expanded profile, including the expansion device contacting the expansion bearing portion and applying an outward expansion force on the expansion bearing portion such that the barb portion extends outside the second expanded profile.

7. A medical device system, comprising:
   an expansion device that is radially expandable to apply an expansion force;
   an expandable medical device having an outer surface and an inner surface, the expandable medical device defining a longitudinal axis and having a first compacted profile and, upon application of the expansion force with the expansion device that is directed radially outwardly relative to the longitudinal axis, a second expanded profile;
   an expandable anchor having a device attachment portion, a barb portion and an expansion bearing portion positioned therebetween;
   the device attachment portion being coupled to;
   wherein prior to the application of the extrinsic force, the barb portion is positioned within the first compacted profile and the expansion bearing portion extends inward relative to the inner surface of the medical device, and
   wherein the expansion bearing portion is configured to be engaged by the expansion device such that the expansion force causes the barb portion to expand such that the barb portion extends outside of the second expanded profile.

8. The system of claim 1 wherein the expandable medical device defines a central longitudinal axis, and further wherein in the first compacted profile the attachment portion extends inwardly toward the longitudinal axis of the expandable medical device.

9. The system of claim 8 wherein in the first compacted profile the barb portion extends outwardly away from the longitudinal axis of the expandable medical device.

10. The system of claim 9 wherein in the first compacted profile the expansion bearing portion extends through an arc between the attachment portion and the barb portion.

11. A medical device system, comprising:
   an expansion device operable to be radially expandable to an expanded state; and
   an expandable medical device mounted to the expansion device for deployment of the expandable medical device, the expandable medical device including a tubular body an expandable anchor having a barb portion and an expansion bearing portion, the tubular body of the expandable medical device having an outer surface and an inner surface, the expandable medical device having a first compacted profile in which the expansion bearing portion extends radially inward from the inner surface of the tubular body and, upon application of an extrinsic force by the expansion device, a second expanded profile, wherein the expansion device is operable to contact the expansion bearing portion to apply an outward extrinsic force on the expansion bearing portion to outwardly displace the expansion bearing portion, wherein in the first compacted profile the barb portion is positioned within the first compacted profile and wherein in the expanded profile, the barb portion extends outside the second expanded profile.

* * * * *